(12) United States Patent
Cormier

(10) Patent No.: US 10,194,833 B2
(45) Date of Patent: Feb. 5, 2019

(54) METHOD AND APPARATUS FOR NON-INVASIVE DETECTION OF CONDITIONS SUCH AS LUNG CANCER

(71) Applicant: Picomole Instruments Inc., Edmonton (CA)

(72) Inventor: John Cormier, Dieppe (CA)

(73) Assignee: Picomole Instruments Inc., Edmonton (CA)

( * ) Notice: Subject to any disclaimer, the term of this patent is extended or adjusted under 35 U.S.C. 154(b) by 221 days.

(21) Appl. No.: 14/720,447

(22) Filed: May 22, 2015

(65) Prior Publication Data

US 2015/0335266 A1 Nov. 26, 2015

Related U.S. Application Data

(60) Provisional application No. 62/002,157, filed on May 22, 2014.

(51) Int. Cl.
*A61B 5/08* (2006.01)
*A61B 5/097* (2006.01)
(Continued)

(52) U.S. Cl.
CPC .............. *A61B 5/082* (2013.01); *A61B 5/097* (2013.01); *G01N 21/3504* (2013.01);
(Continued)

(58) Field of Classification Search
CPC ....... A61B 5/082; A61B 5/097; A61B 5/7271; G01N 21/3504; G01N 33/497;
(Continued)

(56) References Cited

U.S. PATENT DOCUMENTS 5,465,728 A 11/1995 Phillips
6,582,376 B2 6/2003 Baghdassarian
(Continued)

OTHER PUBLICATIONS

Ligor, Magdalena, et al. "Determination of volatile organic compounds in exhaled breath of patients with lung cancer using solid phase microextraction and gas chromatography mass spectrometry." Clinical chemistry and laboratory medicine 47.5 (2009): 550-560.*

(Continued)

*Primary Examiner* — Navin Natnithithadha
*Assistant Examiner* — Andrey Shostak
(74) *Attorney, Agent, or Firm* — Marsh Fischmann & Breyfogle LLP; Jonathon A. Szumny

(57) ABSTRACT

A method of determining whether a subject is likely to have a condition includes measuring concentration levels of a plurality of target biomarkers in a sample obtained from the subject; comparing the measured concentration levels to respective reference concentration levels; in the event that the measured concentration level of at least one of the target biomarkers is less than its respective reference concentration level, and the measured concentration level of at least one of the target biomarkers is greater than its respective reference concentration level, providing an indication that the subject is likely to have the condition, and otherwise: providing an indication that the subject is unlikely to have the condition.

6 Claims, 1 Drawing Sheet

(51) Int. Cl.
  *G01N 21/3504* (2014.01)
  *G01N 33/497* (2006.01)
  *A61B 5/00* (2006.01)
(52) U.S. Cl.
  CPC .......... *G01N 33/497* (2013.01); *A61B 5/7271* (2013.01); *G01N 2033/4975* (2013.01); *G01N 2800/12* (2013.01); *G01N 2800/7028* (2013.01)
(58) Field of Classification Search
  CPC ... G01N 2033/4975; G01N 2800/7028; G01N 2800/12; G06F 19/345
  See application file for complete search history.

(56) References Cited

U.S. PATENT DOCUMENTS

| | | | |
|---|---|---|---|
| 6,726,637 | B2 | 4/2004 | Phillips |
| 8,288,727 | B2 | 10/2012 | Cormier et al. |
| 2004/0162500 | A1 | 8/2004 | Kline |
| 2008/0091085 | A1* | 4/2008 | Urushihata ........ A61B 10/0045 600/300 |
| 2010/0002234 | A1* | 1/2010 | Cormier ................. G01N 21/39 356/436 |
| 2011/0269632 | A1* | 11/2011 | Haick .................... B82Y 15/00 506/7 |
| 2012/0143805 | A1* | 6/2012 | Gold .................... G01N 33/574 706/20 |

OTHER PUBLICATIONS

Vaughan, Christina, et al. "Automated determination of seven phenolic compounds in mainstream tobacco smoke." Nicotine & Tobacco Research10.7 (2008): 1261-1268.*
Fuchs, D., et al. "Decline of exhaled isoprene in lung cancer patients correlates with immune activation." Journal of breath research 6.2 (2012): 027101.*
Cope, et al., "Effects of ventilation on the collection of exhaled breath in humans", J App I Physiol 96: 1371-1379, 2004.

* cited by examiner

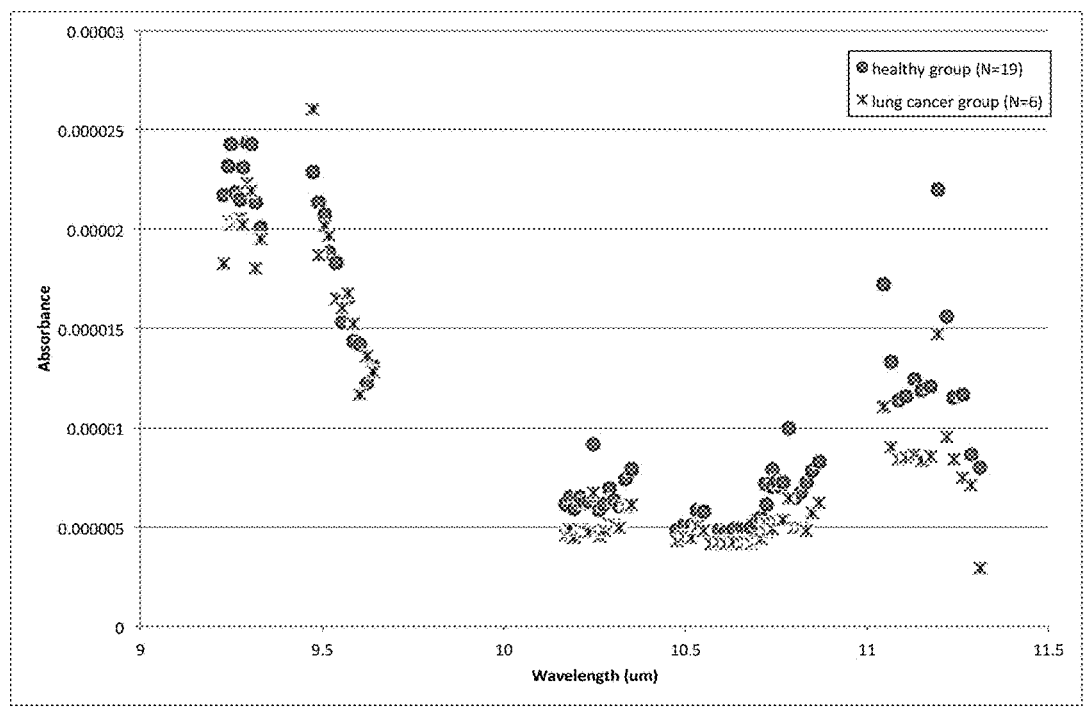

METHOD AND APPARATUS FOR NON-INVASIVE DETECTION OF CONDITIONS SUCH AS LUNG CANCER

CROSS-REFERENCE TO RELATED APPLICATION

This application claims the benefit of U.S. Provisional Patent Application Ser. No. 62/002,157, filed on May 22, 2014 and entitled "METHOD AND APPARATUS FOR NON-INVASIVE DETECTION OF CONDITIONS SUCH AS LUNG CANCER", the contents of which are incorporated herein by reference in its entirety.

FIELD OF THE INVENTION

The following relates generally to the field of medical diagnostics, and more particularly to non-invasive detection of lung cancer using breath samples collected using a breath collection apparatus.

BACKGROUND OF THE INVENTION

The analysis of volatile organic compounds (VOCs) in exhaled human breath is rapidly emerging as a painless, non-invasive alternative to conventional methods of disease diagnosis and metabolite measurement. Breath VOC measurement is also commonly used for monitoring the effects of human exposure to environmental pollutants and drugs.

While hundreds of VOCs have been found in exhaled human breath, many of which originate from blood-air exchange in the lower (i.e. alveolar) area of the lungs, a recent survey by the inventor of more than 1000 published research papers in the field of breath analysis suggests that fewer than 10 percent contain any quantitative data for the chemicals found in exhaled breath samples.

A key advancement in the field of breath analysis has been a full quantitation of VOC results obtained using the analytical technology disclosed in U.S. Pat. No. 8,288,727 to Cormier et al., the contents of which are incorporated herein by reference in their entirety. The technology disclosed in the '727 patent has become known in the art as Laser Infrared Sample Analysis (LISA).

The ability to conduct full quantitation of VOC results with technology such as LISA has facilitated more in-depth and quantifiable research into disease biomarkers.

SUMMARY OF THE INVENTION

In accordance with an aspect, there is provided a method of determining whether a subject is likely to have a condition comprising measuring concentration levels of a plurality of target biomarkers in a sample obtained from the subject; comparing the measured concentration levels to respective reference concentration levels; in the event that the measured concentration level of at least one of the target biomarkers is less than its respective reference concentration level, and the measured concentration level of at least one of the target biomarkers is greater than its respective reference concentration level, providing an indication that the subject is likely to have the condition, and otherwise: providing an indication that the subject is unlikely to have the condition.

In accordance with another aspect, there is provided a method of determining whether a subject is likely to have lung cancer comprising measuring concentration levels of isoprene, furan, ethyl alcohol, toluene and m-Cresol in a breath sample obtained from the subject; comparing the measured concentration levels to respective reference concentration levels; in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level, providing an indication that the subject is likely to have lung cancer, and otherwise: providing an indication that the subject is unlikely to have lung cancer.

In accordance with another aspect, there is provided a method of determining whether a subject is likely to have a condition comprising measuring concentration levels of a plurality of target biomarkers in a sample obtained from the subject; comparing the measured concentration levels to respective reference concentration levels and providing a condition likelihood score based on whether the measured concentration level of at least one of the target biomarkers is less than its respective reference concentration level, and on whether the measured concentration level of at least one of the target biomarkers is greater than its respective reference concentration level.

In accordance with another aspect, there is provided a method of determining whether a subject is likely to have a condition, the method comprising: using an apparatus having a measurement chamber to determine concentration levels of a plurality of biomarkers based on a measurement of the absorption by a sample from the subject received in the measurement chamber of infrared light emitted into the measurement chamber in a plurality of pulsed, discrete monochromatic frequencies; using a computing system, receiving and comparing the measured concentration levels to respective reference concentration levels; using the computing system, providing an indication that the subject is likely to have the condition in the event that the measured concentration level of at least one of the target biomarkers is less than its respective reference concentration level, and the measured concentration level of at least one of the target biomarkers is greater than its respective reference concentration level.

In accordance with another aspect, there is provided a non-transitory computer readable medium embodying a computer program executable on a computing system for determining whether a subject is likely to have a condition, the computer program comprising: computer program code for receiving concentration levels of a plurality of target biomarkers measured by a measurement apparatus in a sample obtained from the subject; computer program code for comparing the measured concentration levels to respective reference concentration levels; and computer program code for, in the event that the measured concentration level of at least one of the target biomarkers is less than its respective reference concentration level, and the measured concentration level of at least one of the target biomarkers is greater than its respective reference concentration level, providing an indication that the subject is likely to have the condition, and otherwise providing an indication that the subject is unlikely to have the condition.

In accordance with another aspect, there is provided a computing system comprising at least one processor executing instructions for determining whether a subject is likely to have a condition, the at least one processor configured to receive concentration levels measured by a measurement apparatus of a plurality of target biomarkers in a sample obtained from the subject, to compare the measured concentration levels to respective reference concentration levels, and to provide an indication that the subject is likely to have the condition in the event that the measured concentration level of at least one of the target biomarkers is less than its respective reference concentration level, and the measured concentration level of at least one of the target biomarkers is greater than its respective reference concentration level.

In accordance with another aspect, there is provided a method of determining whether a subject is likely to have lung cancer, the method comprising: using an apparatus having a measurement chamber to determine concentration levels of at least isoprene, furan, ethyl alcohol, toluene and m-Cresol based on a measurement of the absorption by a breath sample from the subject received in the measurement chamber of infrared light emitted into the measurement chamber in a plurality of pulsed, discrete monochromatic frequencies; using a computing system, receiving and comparing the measured concentration levels to respective reference concentration levels; using the computing system, providing an indication that the subject is likely to have the condition in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level.

In accordance with another aspect, there is provided a non-transitory computer readable medium embodying a computer program execuTable on a computing system for determining whether a subject is likely to have lung cancer, the computer program comprising: computer program code for receiving concentration levels of isoprene, furan, ethyl alcohol, toluene and m-Cresol measured by a measurement apparatus in a breath sample obtained from the subject; computer program code for comparing the measured concentration levels to respective reference concentration levels; and computer program code for, in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level, providing an indication that the subject is likely to have lung cancer, and otherwise providing an indication that the subject is unlikely to have lung cancer.

In accordance with another aspect, there is provided a computing system comprising at least one processor executing instructions for determining whether a subject is likely to have lung cancer, the at least one processor configured to receive concentration levels measured by a measurement apparatus of isoprene, furan, ethyl alcohol, toluene and m-Cresol in a breath sample obtained from the subject, to compare the measured concentration levels to respective reference concentration levels, and to provide an indication that the subject is likely to have the condition in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level.

Other aspects and advantages will become apparent from the following description and drawings.

BRIEF DESCRIPTION OF THE DRAWINGS

Embodiments of the invention will now be described with reference to the appended drawing in which:

FIG. 1 is a graph showing infrared absorption spectrum of exhaled breath as a function of probe wavelength.

DETAILED DESCRIPTION

A non-invasive method to detect the presence of lung cancer in persons using the collection of exhaled breath samples is disclosed.

The present invention discloses that exhaled breath samples of lung cancer patients have infrared absorption spectra that differ materially from the exhaled breath samples of non-lung cancer control groups. One unexpected finding was that we measured less absorption at many infrared wavelengths for the exhaled breath samples of patients diagnosed with lung cancer than we did for the exhaled breath samples of healthy controls.

The chemicals that contribute the most to the observed infrared spectra of the exhaled breath samples are identified and quantified.

A preliminary non-invasive diagnostic test for lung cancer derived from the concentrations of a subset of the chemicals responsible for the distinctiveness of the infrared spectra of the exhaled breath samples from lung cancer patients is disclosed.

A clinical study was undertaken to determine if measurements of exhaled breath components using LISA technology are feasible in clinically acquired samples and whether such measurements can be used as an early detection and diagnostic tool for lung cancer.

The inclusion criteria for the study were the following: (a) Adults older than 18; (b) Subjects with one of the following: Primary lung cancer at any stage (Group 1), Chronic lung condition, e.g., asthma, emphysema, bronchitis (Group 2), No known current lung cancer or chronic lung pathology (Group 3), Subjects who have had lung cancer that was successfully treated at least three years prior to consent and who are currently recurrence-free may be considered eligible for the healthy group; (c) Willing and physically able to provide a breath sample; and (d) Willing to sign informed consent.

The exclusion criteria for the study were the following: (a) Subjects known to be infected with an etiological agent (e.g., HIV, hepatitis); (b) Subjects with an acute respiratory infection (i.e., viral, bacterial) or other acute respiratory condition at time of breath collection; (c) Subjects with any other active malignancy within three years of enrollment; (d) Subjects unwilling to sign informed consent.

The exhaled breath samples of the study were all collected at the same respirology clinic using a breath collection apparatus that is described in U.S. Provisional Patent Application Ser. No. 62/002,159, filed May 22, 2014 entitled "ALVEOLAR BREATH COLLECTION APPARATUS".

The alveolar breath samples were automatically transferred to Chromosorb-106 sorbent tubes using the above-noted breath collection apparatus. The sorbent tubes were then shipped to a laboratory for analysis using the above-noted LISA technology.

During collection of each of the exhaled breath samples, samples of the ambient air in the same location were also collected in sorbent tubes, thereby to facilitate further tests to determine if the VOCs measured in the exhaled breath were produced endogenously or were the result of the inhalation of ambient air in the respirology clinic. It is to be noted however that the calculations for the results set forth below did not take into account the ambient air samples collected at the same time. Because all samples were taken from the same respirology clinic, it is expected that taking the ambient air samples into account would not produce results that are markedly different, since each of the collected breath samples would have the respirology clinic's ambient air in common. However, due to the low levels of VOCs being tested, and due to it being known that VOC levels in ambient air in a given location within a building can change over the course of the day (such as increased CO2 levels towards the end of the work day), taking into account the ambient air sample collected at the time of the breath sample may produce results that are somewhat different.

During the study, exhaled breath samples were collected from three groups of human subjects, as shown in Table 1 below:

TABLE 1

| GROUP | NUMBER OF INDIVIDUALS |
|---|---|
| Individuals diagnosed with lung cancer | 11 |
| Individuals diagnosed with other non-cancer lung pathologies | 17 |
| Healthy individuals | 21 |

FIG. 1 is a graph showing infrared absorption spectrum of exhaled breath as a function of probe wavelength. As can be seen from FIG. 1, the infrared absorbance for the healthy group is greater than the infrared absorbance for the lung cancer group at most of the probe wavelengths. In fact, an increase in absorbance in lung cancer exhaled breath versus healthy exhaled breath was observed in only 6 out of the 77 infrared wavelengths that were probed during the study. This reduction in absorption across most of the observed infrared spectrum in exhaled breath samples from lung cancer patients when compared against healthy subjects was not taught in the prior art and was not an expected result.

Once the infrared spectra of all the samples in the clinical study were recorded and archived, the set of chemicals for best modeling the observed infrared spectra of all groups was constructed using a custom computational algorithm and a database of reference infrared spectra of chemicals. At each iteration, the algorithm would either add or subtract one chemical from the current model set of chemicals that best defines the infrared spectra of all groups, based on which chemical whether added or subtracted produced the greatest reduction in the mean residual of the profiles for each of the three groups of human subjects.

Some of the chemicals that were quantified in exhaled breath samples are known products of human metabolism, such as ethanol, isoprene, and acetone. Several other research groups have already observed these chemicals in breath. Furthermore, for these chemicals, the concentrations that were measured during the study in the exhaled breath samples of healthy human subjects were found to be in agreement with the values reported in the peer-reviewed scientific literature to within experimental errors.

These chemicals, along with dozens of other chemicals, were identified and quantified in each breath sample. No other infrared-based analytical technology has demonstrated the ability that LISA technology has to simultaneously identify and quantify as many chemicals in exhaled breath samples.

Using quantitative data for the chemicals found in the exhaled breath samples of the three groups in our study, a novel methodology to test for the presence of diseases such as lung cancer has been developed.

Table 2 lists the chemicals that were detected in more than 50% of the exhaled breath samples during the study, with the exclusion of a few low-mass chemicals such as carbon dioxide and water vapor for which the Chromosorb-106 sorbent tube does not have a high affinity, and furthermore are not considered to have important diagnostic potential. The median concentrations (in parts-per-billion, or ppb) are presented for the healthy group and for the lung cancer group.

TABLE 2

| Chemical | CAS # | healthy (ppb) | lung cancer (ppb) | regulation |
|---|---|---|---|---|
| 1-Hexanoic acid | 142-62-1 | 75 | 58 | down |
| 1-Pentene | 109-67-1 | 0.92 | 0.99 | up |
| 2-Methylpentane | 107-83-5 | 28 | 34 | up |
| 2-Pentanol | 6032-29-7 | 0.14 | 0.14 | n.s. |
| Acetaldehyde | 75-07-0 | 52 | 40 | down |
| Acetone | 67-64-1 | 630 | 590 | down |
| Acetonitrile | 75-05-8 | 16 | 15 | down |
| Benzaldehyde | 100-52-7 | 0.93 | 0.93 | n.s. |
| Benzene | 71-43-2 | 8 | 2.7 | down |
| Butyl acetate | 123-86-4 | 1.9 | 1.4 | down |
| Carbonyl sulfide | 463-58-1 | 200 | 170 | n.s. |
| Cyclohexane | 110-82-7 | 1.9 | 2 | n.s. |
| Cyclohexanol | 108-93-0 | 0.15 | 0.34 | up |
| Cyclohexanone | 108-94-1 | 0.8 | 0.9 | up |
| Decane | 124-18-5 | 5.3 | 4.8 | down |
| Ethyl alcohol | 64-17-5 | 89 | 160 | up |
| Ethyl benzene | 100-41-4 | 0.5 | 0.5 | n.s. |
| Ethyl mercaptan | 75-08-1 | 3.4 | 3.3 | up |
| Ethylene | 74-85-1 | 2.7 | 2.3 | down |
| Formaldehyde | 50-00-0 | 11 | 8.7 | down |
| Formic acid | 64-18-6 | 13 | 25 | down |
| Furan | 110-00-9 | 28 | 23 | down |
| Isobutenal | 78-85-3 | 2.1 | 0.98 | down |
| Isoprene | 78-79-5 | 120 | 62 | down |
| Isopropyl alcohol | 67-63-0 | 25 | 18 | down |
| m-Cresol | 108-39-4 | 5 | 5.5 | up |
| Methyl alcohol | 67-56-1 | 53 | 34 | down |
| Methyl chloride | 74-87-3 | 1.4 | 1.2 | down |
| Methyl ethyl ketone | 78-93-3 | 5.3 | 5.4 | n.s. |
| Methyl mercaptan | 74-93-1 | 2.4 | 2.6 | up |
| Pentane | 109-66-0 | 16 | 18 | up |
| Phenol | 108-95-2 | 5.2 | 5.3 | n.s. |
| Propane | 74-98-6 | 14 | 16 | up |
| Propionaldehyde | 123-38-6 | 7.2 | 7.2 | n.s. |
| Propyl acetate | 109-60-4 | 0.32 | 0.22 | down |
| Styrene | 100-42-5 | 0.43 | 0.44 | up |
| Sulfur hexafluoride | 2551-62-4 | 0.009 | 0.008 | n.s. |
| Toluene | 108-88-3 | 4.7 | 6 | up |
| Trichlorofluoromethane | 75-69-4 | 0.036 | 0.033 | down |
| Trimethylamine | 75-50-3 | 36 | 33 | up |
| Undecane | 1120-21-4 | 3 | 2.8 | up |
| 1-Hexene | 592-41-6 | n.q | n.q | — |
| Dichloromethane | 75-09-2 | n.q | n.q | — |
| Heptane | 142-82-5 | n.q | n.q | — |

TABLE 2-continued

| Chemical | CAS # | healthy (ppb) | lung cancer (ppb) | regulation |
|---|---|---|---|---|
| Hexane | 110-54-3 | n.q | n.q | — |
| Isobutane | 75-28-5 | n.q | n.q | — |
| Isocumene | 103-65-1 | n.q | n.q | — |
| Trichloroethylene | 79-01-6 | n.q | n.q | — |

A careful examination of the quantitative data led to a conclusion that several of the chemicals listed in Table 2 have diagnostic potential for the detection of lung cancer. Many of these have not been reported to be linked to lung cancer in the prior art.

The general approach to utilizing the quantitative data during the study is as follows. First, threshold levels that could be used to discriminate between groups were determined from the exhaled breath concentrations of select chemicals. It was considered that a test for a given disease would be positive if the chemicals comprising the test all meet the required criteria relative to the threshold level. Otherwise the test would be negative. A number of different ways to construct useful diagnostic tests for lung cancer were experimented with using the captured data. For example, a diagnostic test for lung cancer was constructed using only a set of chemicals that appeared to be upregulated (elevated concentration) in subjects diagnosed with lung cancer. Similarly, a diagnostic test for lung cancer was constructed using only a set of chemicals that appeared to be down-regulated (reduced concentration) in subjects diagnosed with lung cancer.

On the basis that the best test for lung cancer is a test that provides the greatest sensitivity and specificity, while requiring the fewest number of chemicals, a simple yet powerful test for lung cancer was developed. This was done by careful selection of a combination of chemicals that were shown during the study to upregulate and other chemicals that were shown during the study to down-regulate.

According to one embodiment, the test for lung cancer has just 5 criteria, as summarized in Table 3 below:

TABLE 3

| Chemical | Threshold (ppb) | Criteria |
|---|---|---|
| Isoprene | 93.2 | Less than threshold |
| Furan | 23.7 | Less than threshold |
| Ethyl alcohol | 33.7 | Greater than threshold |
| Toluene | 2.6 | Greater than threshold |
| m-Cresol | 3.1 | Greater than threshold |

The test for lung cancer is considered to be positive only if all five of the criteria in Table 3 are met. Otherwise, the test is negative.

The diagnostic potential of this test for lung cancer is demonstrated using the results from the three groups in the study: The sensitivity to lung cancer is 100% (6 of 6 subjects in the lung cancer group tested positive), while the specificity is 97.1% (33 of 34 subjects in the non-lung cancer groups tested negative).

While the above-described test for lung cancer is derived from the minimum set of chemicals needed to achieve the reported sensitivity and specificity, in an alternative embodiment the test could be expanded to include other chemicals from the list in Table 2 in order to preserve accuracy, for example as a result of factors introduced from a larger study.

Although all of the subjects included in the study above were current non-smokers, the above-described test for lung cancer was tried on two healthy volunteer smokers. In both cases, the test was negative, raising the possibility that our breath test for lung cancer could be administered to active smokers without significant loss of accuracy.

The smokers were segregated in the study from the non-smokers due to the fact that breath profiles of smokers can be very difficult to interpret. However, with the integration of the smokers into the analysis, it was found that the threshold values for three of the five chemicals in Table 3 could be adjusted as shown in Table 4 below.

TABLE 4

| Chemical | Threshold (ppb) | Criteria |
|---|---|---|
| Isoprene | 104.9 | Less than threshold |
| Furan | 25.6 | Less than threshold |
| Ethyl alcohol | 33.7 | Greater than threshold |
| Toluene | 1.89 | Greater than threshold |
| m-Cresol | 3.1 | Greater than threshold |

With the smokers' results having been integrated, the following metrics are achieved for the lung cancer test: sensitivity 90.9% (10 of 11 of lung cancer group including smokers test positive) specificity 94.7% (36 of 38 of non-lung cancer groups including smokers test negative).

The results suggest an average overall accuracy of 92.8% when both smokers and non-smokers are included in the analysis. For smokers alone, the sensitivity is 80% (4 of 5 test positive) and the specificity is 100% (4 of 4 test negative), implying a test accuracy of 90% for smokers.

Based on the above findings, methods, a computing system and computer readable media embodying computer readable program code were developed. In general, a method of determining whether a subject is likely to have a condition includes measuring concentration levels of a plurality of target biomarkers in a sample obtained from the subject; comparing the measured concentration levels to respective reference concentration levels; in the event that the measured concentration level of at least one of the target biomarkers is less than its respective reference concentration level, and the measured concentration level of at least one of the target biomarkers is greater than its respective reference concentration level, providing an indication that the subject is likely to have the condition, and otherwise providing an indication that the subject is unlikely to have the condition.

In an embodiment, the sample is a breath sample, and measuring the concentration levels includes receiving the breath sample within a measurement chamber; and determining the concentration levels based on a measurement of the absorption by the breath sample of infrared light emitted into the measurement chamber in a plurality of pulsed, discrete monochromatic frequencies.

An apparatus such as that disclosed in U.S. Pat. No. 8,288,727 to Cormier et al., referred to above, provides an appropriate measurement chamber, a source of infrared light, and other components for measuring concentration levels and making the concentration levels available to a processing device for downstream processing.

In an embodiment, a method of determining whether a subject is likely to have lung cancer includes measuring concentration levels of isoprene, furan, ethyl alcohol, toluene and m-Cresol in a breath sample obtained from the subject; comparing the measured concentration levels to respective reference concentration levels; in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level, providing an indication that the subject is likely to have lung cancer, and otherwise providing an indication that the subject is unlikely to have lung cancer.

In an embodiment, measuring the concentration levels includes receiving the breath sample within a measurement chamber; and determining the concentration levels based on a measurement of the absorption by the breath sample of infrared light emitted into the measurement chamber in a plurality of pulsed, discrete monochromatic frequencies. An apparatus such as that disclosed in U.S. Pat. No. 8,288,727 to Cormier et al, referred to above, provides an appropriate measurement chamber, source of infrared light, and other components for measuring concentration levels and making the concentration levels available to a processing device for downstream processing.

In another embodiment, a method of determining whether a subject is likely to have a condition includes measuring concentration levels of a plurality of target biomarkers in a sample obtained from the subject; and comparing the measured concentration levels to respective reference concentration levels and providing a condition likelihood score based on whether the measured concentration level of at least one of the target biomarkers is less than its respective reference concentration level, and on whether the measured concentration level of at least one of the target biomarkers is greater than its respective reference concentration level.

In another embodiment, there is provided a method of determining whether a subject is likely to have a condition, the method comprising using an apparatus having a measurement chamber to determine concentration levels of a plurality of biomarkers based on a measurement of the absorption by a sample from the subject received in the measurement chamber of infrared light emitted into the measurement chamber in a plurality of pulsed, discrete monochromatic frequencies; using a computing system, receiving and comparing the measured concentration levels to respective reference concentration levels; using the computing system, providing an indication that the subject is likely to have the condition in the event that the measured concentration level of at least one of the target biomarkers is less than its respective reference concentration level, and the measured concentration level of at least one of the target biomarkers is greater than its respective reference concentration level.

An apparatus such as that disclosed in U.S. Pat. No. 8,288,727 to Cormier et al., referred to above, provides an appropriate measurement chamber, source of infrared light, and other components for measuring concentration levels and making the concentration levels available to a processing device for downstream processing. The computing system may be integrated with or connected to such an apparatus.

In embodiment, the indication provided is an electronic or paper-based report, an electronic signal, an indication displayed on the computing system, or some other indicia.

In another embodiment, there is provided a non-transitory computer readable medium embodying a computer program executable on a computing system for determining whether a subject is likely to have a condition, the computer program including computer program code for receiving concentration levels of a plurality of target biomarkers measured by a measurement apparatus in a sample obtained from the subject; computer program code for comparing the measured concentration levels to respective reference concentration levels; and computer program code for, in the event that the measured concentration level of at least one of the target biomarkers is less than its respective reference concentration level, and the measured concentration level of at least one of the target biomarkers is greater than its respective reference concentration level, providing an indication that the subject is likely to have the condition, and otherwise providing an indication that the subject is unlikely to have the condition.

The computer program may be executed on a computing system that is integrated with or connected to an apparatus such as that disclosed in U.S. Pat. No. 8,288,727 to Cormier et al., referred to above.

A computer readable medium providing instructions to a processor or processing structure of a computing system may take many forms, including but not limited to, non-volatile media, volatile media, and transmission media. Non-volatile media includes, for example, optical, magnetic disks, and magneto-optical disks, such as a hard disk or a removable media drive. Volatile media includes dynamic memory. Various forms of computer readable media may be involved in carrying out one or more sequences of one or more instructions to a processor for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computing system may receive the data on the telephone line and use an infrared transmitter to convert the data to an infrared signal. An infrared detector coupled to a computing bus can receive the data carried in the infrared signal and place the data on the bus. The bus carries the data to the main memory, from which the processor or processing structure retrieves and executes the instructions. The instructions received by the main memory may optionally be stored on a storage device either before or after execution by a processor or processing structure.

In another embodiment, there is provided a computing system comprising at least one processor executing instructions for determining whether a subject is likely to have a condition, the at least one processor configured to receive concentration levels measured by a measurement apparatus of a plurality of target biomarkers in a sample obtained from the subject, to compare the measured concentration levels to respective reference concentration levels, and to provide an indication that the subject is likely to have the condition in the event that the measured concentration level of at least one of the target biomarkers is less than its respective reference concentration level, and the measured concentration level of at least one of the target biomarkers is greater than its respective reference concentration level.

The computing system may be integrated with or connected to an apparatus such as that disclosed in U.S. Pat. No. 8,288,727 to Cormier et al, referred to above.

In another embodiment, there is provided a method of determining whether a subject is likely to have lung cancer, the method comprising using an apparatus having a measurement chamber to determine concentration levels of at least isoprene, furan, ethyl alcohol, toluene and m-Cresol based on a measurement of the absorption by a breath sample from the subject received in the measurement chamber of infrared light emitted into the measurement chamber in a plurality of pulsed, discrete monochromatic frequencies;

using a computing system, receiving and comparing the measured concentration levels to respective reference concentration levels; using the computing system, providing an indication that the subject is likely to have the condition in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level.

An apparatus such as that disclosed in U.S. Pat. No. 8,288,727 to Cormier et al., referred to above, provides an appropriate measurement chamber, source of infrared light, and other components for measuring concentration levels and making the concentration levels available to a processing device for downstream processing. The computing system may be integrated with or connected to such an apparatus.

In another embodiment, there is provided a non-transitory computer readable medium embodying a computer program executable on a computing system for determining whether a subject is likely to have lung cancer, the computer program comprising computer program code for receiving concentration levels of isoprene, furan, ethyl alcohol, toluene and m-Cresol measured by a measurement apparatus in a breath sample obtained from the subject; computer program code for comparing the measured concentration levels to respective reference concentration levels; and computer program code for, in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level, providing an indication that the subject is likely to have lung cancer, and otherwise providing an indication that the subject is unlikely to have lung cancer.

The computer program may be executed on a computing system that is integrated with or connected to an apparatus such as that disclosed in U.S. Pat. No. 8,288,727 to Cormier et al., referred to above.

In another embodiment, there is provided a computing system comprising at least one processor executing instructions for determining whether a subject is likely to have lung cancer, the at least one processor configured to receive concentration levels measured by a measurement apparatus of isoprene, furan, ethyl alcohol, toluene and m-Cresol in a breath sample obtained from the subject, to compare the measured concentration levels to respective reference concentration levels, and to provide an indication that the subject is likely to have the condition in the event that the measured concentration level of isoprene is less than a respective reference concentration level, and the measured concentration level of furan is less than a respective reference concentration level, and the measured concentration level of ethyl alcohol is greater than a respective reference concentration level, and the measured concentration level of toluene is greater than a respective reference concentration level, and the measured concentration level of m-Cresol is greater than a respective reference concentration level.

The computing system may be integrated with or connected to an apparatus such as that disclosed in U.S. Pat. No. 8,288,727 to Cormier et al, referred to above.

It is expected that the threshold values for each chemical may require adjustments as follow-on studies are conducted with larger and different populations. There is also the potential that a test better suited to smokers could be constructed from a different set of chemicals. This may be determined through larger studies involving more smokers.

Furthermore, as discussed above, the threshold values may be affected by variations in the ambient levels where the samples are collected. Accounting for ambient levels, a focus of ongoing research efforts, could also lead to the selection of different chemicals for the test.

Although embodiments have been described with reference to the drawings, those of skill in the art will appreciate that variations and modifications may be made without departing from the spirit, scope and purpose of the invention as defined by the appended claims.

What is claimed is:

1. An automated computer-implemented method of rapidly detecting a combination of up- and down-regulated target biomarkers in a breath sample of an individual, the combination of target biomarkers being indicative of the presence of lung cancer, the method comprising:
    providing a computer processor operative to determine whether the individual is likely to have lung cancer based on a concentration level for each of the target biomarkers, wherein the target biomarkers consist of isoprene, furan, ethyl alcohol, toluene and m-Cresol,
    obtaining the breath sample from the individual,
    emitting infrared light through the sample and measuring the infrared light absorbance values of the sample to detect the presence of the target biomarkers, the light absorbance values being indicative of the concentration level for each of the detected target biomarkers,
    determining which of the detected target biomarkers has a concentration level that is less than a respective threshold reference infrared absorption value and which of the detected target biomarkers has a concentration level that is greater than its respective threshold reference value,
    where the combination of target biomarkers having lower concentration levels and target biomarkers having greater concentration levels is indicative of the presence of lung cancer, and
    displaying, at the computer processor, the indicated presence of lung cancer to the individual.

2. The method of claim 1, wherein the target biomarkers that are down-regulated are isoprene and furan.

3. The method of claim 1, wherein the target biomarkers that are up-regulated are ethyl alcohol, toluene, and m-Cresol.

4. The method of claim 1, wherein the combination indicative of the presence of lung cancer consists of the detected concentration levels of isoprene and furan being less than their respective threshold reference values, and the detected concentration levels of ethyl alcohol, toluene and m-Cresol being greater than their respective threshold reference values.

5. The method of claim 1, wherein the infrared light is emitted in a plurality of pulsed, discrete monochromatic frequencies.

6. An automated computer-implemented method of rapidly detecting a combination of up- and down-regulated target biomarkers in a breath sample of an individual, the combination of target biomarkers being indicative of the presence of lung cancer, the method comprising:

provide a computer processor operative to determine whether the individual is likely to have lung cancer based on a concentration level for each of the target biomarkers, wherein the target biomarkers consist of isoprene, furan, ethyl alcohol, toluene and m-Cresol, obtaining the breath sample from the individual, emitting infrared light through the sample and measuring the infrared light absorbance values of the sample to detect the presence of the target biomarkers, the light absorbance values being indicative of the concentration level for each of the detected target biomarkers, determining which of the detected target biomarkers has a concentration level that is less than a respective threshold reference infrared absorption value and which of the detected target biomarkers has a concentration level that is greater than its respective threshold reference value, and displaying, at the computer processor, the indicated presence of lung cancer to the individual, wherein the combination indicative of the presence of lung cancer consists of the detected concentration levels of isoprene and furan being less than their respective threshold reference values, and the detected concentration levels of ethyl alcohol, toluene and m-Cresol being greater than their respective threshold reference values.

* * * * *